United States Patent
Ballesteros García et al.

(10) Patent No.: US 6,596,258 B1
(45) Date of Patent: Jul. 22, 2003

(54) METHOD OF OBTAINING EXTRACELLULAR AND INTRACELLULAR PH IMAGES AND SPECTRA BY MAGNETIC RESONANCE USING EXTRINSIC INDICATORS CONTAINING $^1$H OR $^{19}$F

(75) Inventors: Paloma Ballesteros García, Madrid (ES); M$^a$ Soledad Gil González, Madrid (ES); Paula Zaderenco Partida, Madrid (ES); Sebastián Cerdán García-Esteller, Madrid (ES); José Álvarez Pérez, Madrid (ES); J. Robert Gillies, Tucson, AZ (US); Raghunand Natarajan, Tucson, AZ (US); Robert Van Sluis, Tucson, AZ (US); Zaver Bhujwala, Baltimore, MD (US)

(73) Assignee: Universidad Nacional de Educacion a Distancia, Madrid (ES)

( * ) Notice: Subject to any disclaimer, the term of this patent is extended or adjusted under 35 U.S.C. 154(b) by 0 days.

(21) Appl. No.: 09/380,677

(22) PCT Filed: Feb. 26, 1998

(86) PCT No.: PCT/ES98/00045
§ 371 (c)(1),
(2), (4) Date: Jun. 7, 2000

(87) PCT Pub. No.: WO98/39664
PCT Pub. Date: Sep. 11, 1998

(30) Foreign Application Priority Data

Mar. 6, 1997 (ES) .............................. 9700496

(51) Int. Cl.$^7$ .......................... A61B 5/055; G01N 24/00
(52) U.S. Cl. ...................... 424/9.3; 424/9.37; 436/173
(58) Field of Search ................ 424/9.3, 9.37; 436/173

(56) References Cited

U.S. PATENT DOCUMENTS

5,639,906 A    6/1997    London et al.

FOREIGN PATENT DOCUMENTS

| EP | 0095124 | 5/1983 |
| EP | 0368429 | 10/1989 |
| WO | WO 93/03771 | 3/1993 |
| WO | WO 95/17910 | 7/1995 |
| WO | WO 96/04249 | 2/1996 |

OTHER PUBLICATIONS

Bhawalpur, 1988, Chemical Abstract, 110: No.: 212693 t.
Gil et al., 1994, Bioorg Med Chem, 2:305–14.
Gil et al., 1992, Bioorg Med Chem Lett, 2:1717–22.
Kirk et al., 1971, J Am Chem Soc, 93:3060–1.
Pan et al., 1988, Proc Natl Acad Sci USA, 85:7836–9.
van Sluis et al., 1999, Magnetic Resonance in Medicine, 41:743–50.
Yoshizaki et al., 1981, Biochimica et Biophysica Acta, 678:283–91.
Zaderenlo et al., 1994, J org Chem, 59:6268–73.

*Primary Examiner*—Michael G. Hartley
(74) *Attorney, Agent, or Firm*—Klauber & Jackson

(57) ABSTRACT

The present invention refers to the use of a selection of imidazole compounds in a method of obtaining extracellular or intracellular pH images in biological systems, by magnetic resonance, consisting of administering the imidazole compound to said biological system and acquiring a pH image through magnetic resonance measurements, and said method selected from the group consisting of proton magnetic resonance chemical shift imaging ($^1$H CSI), proton magnetic resonance spectroscopic imaging ($^1$H MRSI), fluorine magnetic resonance chemical shift imaging ($^{19}$F CSI), fluorine magnetic resonance spectroscopic imaging ($^{19}$F MRSI), and combinations thereof.

13 Claims, 4 Drawing Sheets

Figure 1:
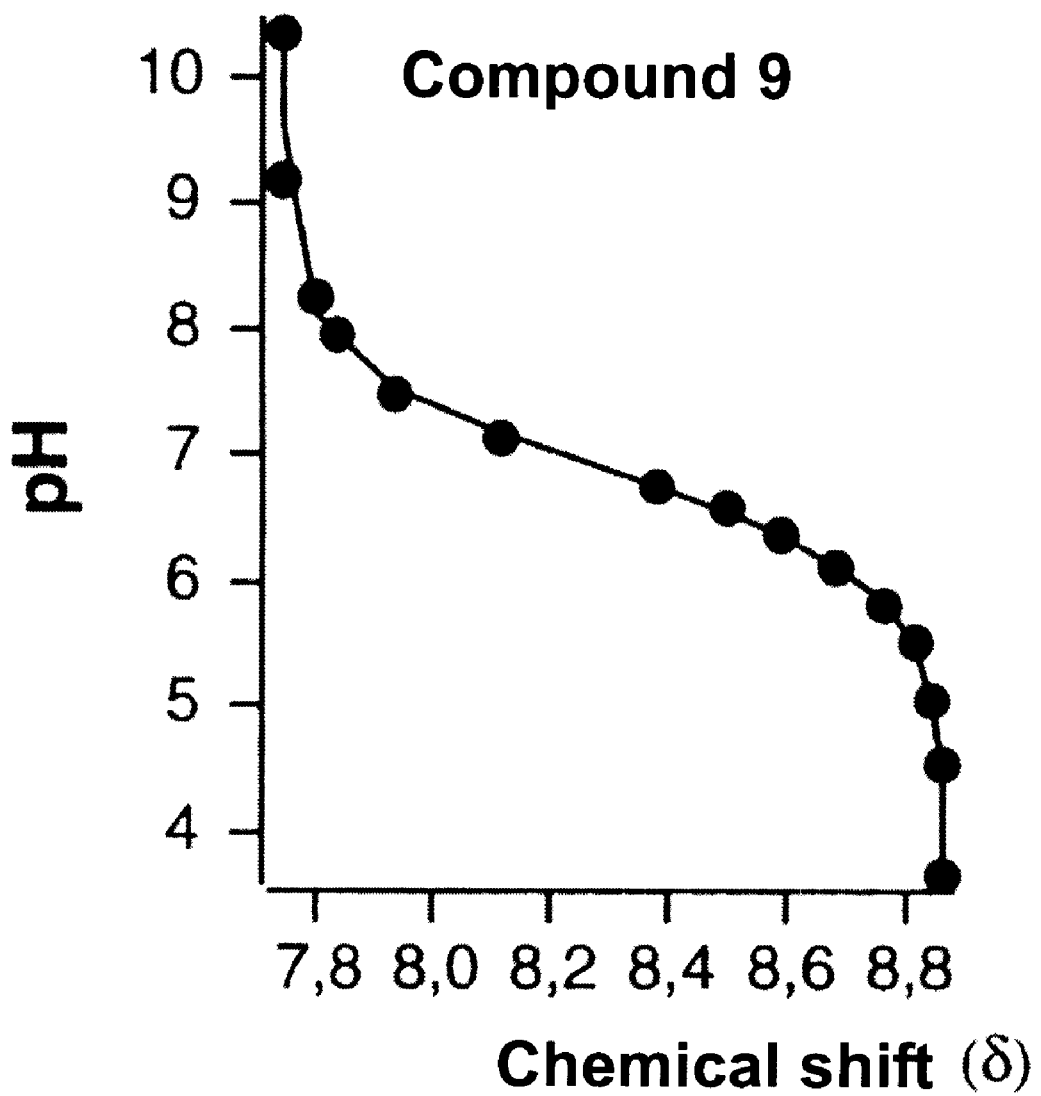

METHOD OF OBTAINING EXTRACELLULAR AND INTRACELLULAR PH IMAGES AND SPECTRA BY MAGNETIC RESONANCE USING EXTRINSIC INDICATORS CONTAINING $^1$H OR $^{19}$F

This application is a 371 of PCT/ES98/00045, filed Feb. 26, 1998.

TECHNICAL AREA

Physical Medicine

Pharmacy

Biomedical Research

Imaging Diagnostics

STATE OF THE ART

The biomedical applications of Magnetic Resonance (MR) have experienced an important development over the last few decades (Andrew, E. R., Byders, G., Griffiths, J., Iles, R. and Styles, P. Eds (1990) *Clinical Magnetic Resonance Imaging and Spectroscopy.* John Wiley and Sons. New York) Both Magnetic Resonance Spectroscopy (MRS) and Imaging (MRI) have been used for non-invasive studies on both animal and human pathological and physiological processes (Gillies, R. J. Ed. (1994) *NMR in Physiology and Biomedicine,* Academic Press, New York). Further, it has been possible to extend the applications of MR to study pathological and physiological processes at the cell level (Gillies, R. J., Gallons, J. P., McGovern, K. A., Scherrer, P. G., Lien, Y. H., Job, C. R., Chapa, F., Cerdan, S. and Dale, B. E. (1993) NMR in *Biomedicine* 6,95–104). Taken together, these advances have permitted to apply MR to study some fundamental aspects of Biology and Medicine, like cellular proliferation and differentiation, or tumoral transformation. These processes do occur with accompanying changes in intra and extracellular pH. Further, pH is a crucial physiological variable in other fundamental processes such as physical exercise and muscle fatigue, metabolic control, and hormonal message transduction (Roos, A. and Boron, W. F. (1981) *Physiol. Rev* 61, 296–696).

The intracellular proton concentration results from a balance between a number of factors including the intracellular proton production and consumption, proton uptake from and extrusion to the extracellular medium, and the intracellular proton buffering capacity (Molde, M., Cruz, F., Chapa, F., Cerdan, F. and Cerdan, S. (1995) *Quart. Mag. Res. in Biol. Med.* 2, 5–17). Considering that the latter is fairly constant under normal conditions, an increase in intracellular proton production may be balanced by either acid extrusion to or base uptake from the extracellular medium; whereas an increased intracellular base production could be compensated by the opposite mechanism. Thus, changes in extracellular pH normally reflect a change in intracellular pH, and measuring extracellular pH provides a useful mean to monitor any alteration in intracellular pH homeostasis.

Methods currently available for pH determination in biological samples include potentiometric methods (pH electrodes), radiometric techniques, optical methods and Magnetic Resonance (Henderson, R. M. and Graf, J. (1988). In pH Homeostasis: Mechanisms and Control (Häussinger, D. Ed.) Academic Press, pg. 5–26). In principle, any of these procedures is able to measure exclusively extracellular pH, provided that a non-permeable molecular probe, be it radioactive, chromophoric, fluorescent, phosphorescent, or active in the case of MR, is used. However, among all these methods, only MR allows one to collect non-invasive images from the entire volume of optically opaque samples. For this reason, MR is the most suitable method for non-invasive determinations of extracellular pH in biological specimens. In this patent we describe the use and applications of a new series of indicator molecules, which allow determining the intracellular and extracellular pH, using the MRS and MRI methods.

Previous approaches have mainly used $^{31}$P MRS and chemical shift of the inorganic phosphate to measure intracellular pH in cellular suspensions, perfused organs, tissue samples, intact animals and even human beings (Moon, R. B. and Richards, J. H. (1973) *J. Biol. Chem.* 248, 7276–7278). A variation of this method applied to cell suspensions has made possible 1D-$^{31}$P MRS measurements of the extracellular pH exclusively, by using phosphonates non-permeable to the plasma membrane (Guillies, R. J., Liu, Z. and Bhujawalla, Z. (1994) *Am. J. Physiol.* 267, C195–C203). On the other hand, localized $^{31}$P MRS techniques to obtain $^{31}$P NMR spectra from a restricted spatial region (voxel) within an intact animal, and thus determine the average intracellular pH for that particular region, using $P_i$ chemical shift, have been previously reported (Aue, W. P. (1986) *Rev. Mag. Res. Med.* 1, 21–72; Ordidge, R. J., Connelly, A. and Lohman, J. A. B. (1986) *J. Mag. Res.* 66, 283–294; Frahm, J., Bruhn, H., Gyngell, M. N. L., Merboldt, K. D., Hanike, W. and Sauter, R. (1989) *Mag. Res. Med.* 9, 79–93). Multivoxel imaging $^{31}$P MRS methods have also been developed. With these techniques, it is feasible to obtain $^{31}$P NMR spectra simultaneously from a collection of adjacent voxels that completely span the 3-D volume of the specimen, which provides tridimensional maps of pH distribution throughout the sample (Brown, T. R., Kincaid, B. M. and Ugurbil, K. (1982) *Proc. Natl. Acad. Sci. U.S.A.,* 79, 3523–3526; Maudsley, A. A., Hilal, S. K., Perman, W. H. and Simon, H. E. (1983). *J. Mag. Res.* 66, 283–294; Vigneron, D. B., Nelson, S. J., Nat, R., Murphy-Boesch, J., Kelley, D. A. C., Kessler, H. B., Brown, T. R. and Taylor, J. S. (1990) *Radiology* 177:643–649; Shungu, D. C. and Glickson, J. D. (1993) *Mag. Res. in Med.* 30, 661–71; Shungu, D. C. and Glickson, J. D. (1994) *Mag. Res. in Med.* 32, 277–84).

In spite of this progress, the low sensitivity of the $^{31}$P nucleus poses a limiting factor for the application of $^{31}$P MRS to pH determination. Thus, $^{31}$P MRS methods typically require long acquisition times as well as large voxel size, in order to have a good signal to noise ratio. These two requirements greatly reduce the spatial and temporal resolution of pH determination by $^{31}$P MRS. Both limitations can be lessen by using either $^1$H or $^{19}$F, as these nuclei are inherently more sensitive than $^{31}$P in MR (Gadian, D. G. (1982) Nuclear Magnetic Resonance and its applications to living systems. Oxford University Press. Pg. 8). The increased sensibility of $^1$H ($^{19}$F) MRS compared to $^{31}$P MRS would allow one to obtain spectra, or 1-D, 2-D or 3-D images, with a similar signal to noise ratio as those from $^{31}$P MRS, but 4(3), 16(12) or 64(43) times faster. In like manner, using $^1$H ($^{19}$F) MRS it would be possible to obtain a significant reduction in voxel size, by comparison to that required in $^{31}$P MRS acquisition, while keeping the same signal to noise ratio. However, the presence of intrinsic metabolites with the right $^1$H resonance is rather exceptional (Yoshisaki, K., Seo, Y. and Nishikawa, H. (1981) *Biochem. Biophys. Acta* 678, 283–291), and there are no natural metabolites containing $^{16}$F. Consistently and in order to successfully implement the $^1$H or $^{16}$F MRS (or MRI) technique for intracellular pH determination, the use of extrinsic probes containing $^1$H (Rabenstein, D. L. and Isab, A. (1982) *Anal. Biochem.* 121, 423) or $^{16}$F (Deutsch, C., Taylor, J. S. and Wilson, D. F. (1982) Proc. Natl; Acad. Sci; U.S.A., 79, 7944) pH sensitive nuclei is a must.

BRIEF DESCRIPTION OF THE INVENTION

Part of our team has recently reported the synthesis of a new series of indicators for intracellular pH, extracellular pH and cellular volume $^1$H MNR measurements in cellular suspensions (Gil, M. S., Cruz, F., Cerdan, S. and Ballesteros, P. (1992) *Bioorg. Med. Chem. Lett.* 2, 1117–1722; Gil, M. S., Zaderenko, P., Cruz, F., Cerdan, S. and Ballesteros, P. (1994) *Bioorg. Med. Chem.* 2, 305–14; Zaderenko, P., Gil, M. S., Ballesteros, P. and Cerdan, S. (1994) J. Org. Chem. 59, 6268–73). In this patent, we described some pharmacological and toxicological properties of these molecules, in view of their use as pH indicators in cell cultures and intact animals; and we also explain the procedures followed to obtain pH images from both model systems in vitro as well as from mice carrying RIF-1 tumors in vivo. The use of these new indicators, in conjunction with $^1$H MR techniques, such as chemical shift imaging (CSI) or spectroscopic imaging (SI) results in a considerable reduction in acquisition time and a significant resolution increase for pH measurements, when compared with previous methods based on $^{31}$P MR.

DETAILED DESCRIPTION OF THE INVENTION

Diagram 1 shows the structures of some indicator molecules useful for pH determination with $^1$H MRS. Imidazol (1, $R^1=R^2=$H) and imidazol-1-ilacetic acid (4, $R^1=R^2=$H) are the most relevant permeable probes, when simultaneous intra- and extracellular pH determinations are intended; whereas (±)-3-(etoxycarbonyl)-2-imidazol-1-ilpropionic acid (9, $R^1=R^2=$H) is a non-permeable probe for extracellular pH measurements.

Diagram 1

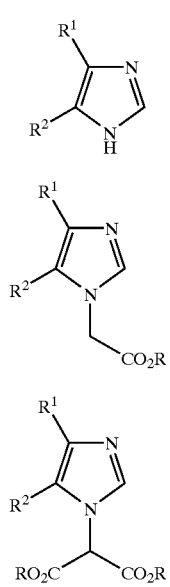

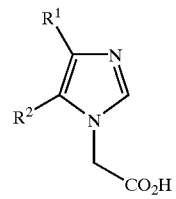

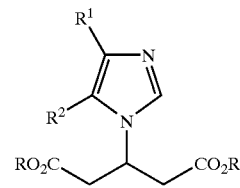

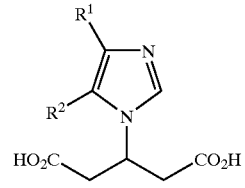

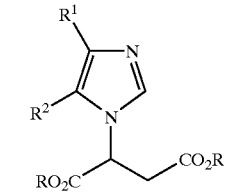

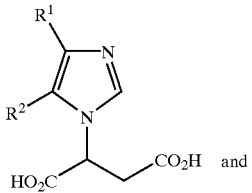

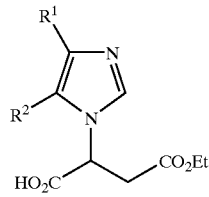

$R^1$ and $R^2$ refer to a hydrogen or any alkyl substitute whether it contains $^{19}$F or no. R represents any alkyl substitute.

The methods to prepare some of these molecules and their NMR properties have been previously described in detail (Gil, M. S., Cruz, F., Cerdan, S. and Ballesteros, P. (1992) *Bioorg. Med. Chem. Lett.* 2, 1117–1722; Gil, M. S., Zaderenko, P., Cruz, F., Cerdan, S. and Ballesteros, P. (1994) *Bioorg. Med. Chem.* 2, 305–14; Zaderenko, P., Gil, M. S., Ballesteros, P. and Cerdan, S. (1994) J. Org. Chem. 59, 6268–73). In general, measuring pH with any of these substances depends upon determining the chemical shift of its H2 proton, which acts as an "informative resonance" in the biological medium, and then comparing it with the chemical shift of this same proton in model solutions of known pH. FIG. 1 shows the relationship between the H2 proton chemical shift of compound 9 ($R^1=R^2=$H, R=Et) and pH. An extension of this procedure consists in obtaining MR images of the H2 proton. These images can be obtained either by selective excitation of H2 and subsequent encoding as images (chemical shift imaging—CSI), or alternatively by non-selective excitation of the entire proton spectrum in adjacent voxels spanning the whole sample (spectroscopic imaging—SI). Both methods reveal the spatial distribution of these compounds H2 resonance within the sample, and hence the pH distribution.

In this invention, we describe the use of these compounds to obtain $^1$H NMR images or spectra which reveal the extracellular pH in many biological systems, including subcellular organelles, isolated or cultured cells from animals or plants, perfused organs, intact animals and human beings. The two last systems, in particular, do require a prior assessment of the potential toxicity and pharmacokinetics of these compounds, in addition to a reliable demonstration of the efficiency of the procedures for pH imaging in vitro and in vivo. The present patent describes: 1) the toxicological properties of some useful probes for measuring extracellular pH, 2) the blood distribution kinetics and tissue uptake for the least toxic compound in this new series and 3) the in vitro and in vivo procedures for both MR chemical shift imaging (CSI) and MR spectroscopic imaging (SI) to collect MR images of extracellular pH in model samples and mice carrying RIF-1 tumors.

Toxicity Studies in Cell Culture and Mice

The toxicity of compounds 5 ($R^1=R^2=H$, R=Et), 6 ($R^1=R^2=H$) and 9 ($R^1=R^2=H$, R=Et) was assessed in cell culture using the procedure described next. NIH 3T3 mouse fibroblasts were grown in Dulbecco modified essential medium (DMEM) supplemented with 10% fetal calf serum (FCS, Hyclone, Logan, Utah, USA). Once confluence was attained, compounds 5 ($R^1=R^2=H$, R=Et), 6 ($R^1=R^2=H$) and 9 ($R^1=R^2=H$, R=Et) were added to the culture medium to obtain a final concentration in the range of 0 to 20 mM. After 72 h incubation, the number of surviving cells in the culture was determined using the method of Gillies and co-workers (Gillies, R. J., Didier, N. and Denton M. (1986) *Anal. Biochem.* 159, 109–113). The results are presented in Table 1. Compound 9 ($R^1=R^2=H$, R=Et) did not exhibit any toxicity, since the number of viable cells in the presence of 20 mM 9 ($R^1=R^2=H$, R=Et) was not significantly different from control (0 mM). Compound 5 ($R^1=R^2=H$, R=Et), however, was very toxic, inducing cell death in almost all cells at 15 mM concentration ($DL_{50}$ 6.8 mM). Finally, compound 6 ($R^1=R^2=H$) proved moderately toxic; it caused a significant reduction in the number of viable cells only at 20 mM, the highest concentration used.

Table 1. Effect of increasing concentrations of compounds 5 ($R^1=R^2=H$, R=Et), 6 ($R^1=R^2=H$) and 9 ($R^1=R^2=H$, R=Et) on cell survival.

| Concentration (mM) | Compound 5 (R1=R$^2$=H, R=Et) | Compound 6 ($R^1=R^2=H$) | Compound 9 (R1=R$^2$=H, R=Et) |
|---|---|---|---|
| 0.0 | 1.54 ± 0.04 | 1.39 ± 0.31 | 1.65 ± 0.12 |
| 1.0 | 1.52 ± 0.10 | 1.50 ± 0.22 | 1.68 ± 0.04 |
| 5.0 | 1.02 ± 0.08 | 1.34 ± 0.11 | 1.38 ± 0.06 |
| 10.0 | 0.37 ± 0.08 | 1.40 ± 0.14 | 1.52 ± 0.13 |
| 15.0 | 0.27 ± 0.01 | 1.29 ± 0.13 | 1.60 ± 0.13 |
| 20.0 | 0.20 ± 0.05 | 1.10 ± 0.06 | 1.54 ± 0.09 |

Cell survival was quantified by measuring the average optical density (an index of cell number) (Gillies, R. J., Didier, N. and Denton M. (1986) *Anal. Biochem.* 159, 109–113) as stated in reference 24. Results represent the mean±SD of four determinations from different culture dishes at each concentration.

The toxicity ($LD_{50}$) of compounds 1 ($R^1=R^2=H$), 4 ($R^1=R^2=H$) and 9 ($R^1=R^2=H$, R=Et) in intact animals was also determined. The results from these experiments are presented in Table 2. Male Swiss albino mice (30–40 g. body weight) were injected intraperitoneally with increasing doses of compounds 1 ($R^1=R^2=H$), 4 ($R^1=R^2=H$) and 9 ($R^1=R^2=H$, R=Et), up to 3 g/Kg body weight. At least seven different doses, each one of then administered to six mice, which were kept in different cages, were used for each compound. The $LD_{50}$ value was determined one week after the injection using the method of Miller and Tainter (Vallette, G. (1966) Manual of Pharmacodynamics. Masson et Cie, Eds. Paris, VIe, pg. 70). Compound 9 ($R^1=R^2=H$, R=Et) which, on the basis of its NMR properties and its behaviour in erythrocyte suspensions is a very useful extracellular pH indicator, did not exhibit any toxicity for doses as high as 3 g/Kg of body weight. Similar results were obtained for compound 4 ($R^1=R^2=H$). Compound 1 ($R^1=R^2=H$), on the other hand, proved toxic in the concentration range assayed, but exhibited a relatively high $DL_{50}$. Hence, compound 9 ($R^1=R^2=H$, R=Et) is endowed with toxicological properties which allow it to be used as an extracellular pH indicator, both in animals and humans.

TABLE 2

| $LD_{50}$ values for compounds 1 ($R^1=R^2=H$), 4 ($R^1=R^2=H$) and 9 ($R^1=R^2=H$, R=Et). | |
|---|---|
| Compound | $LD_{50}$ mg/g body weight |
| 1 ($R^1=R^2=H$) | 250 |
| 4 ($R^1=R^2=H$) | >3000 |
| 9 ($R^1=R^2=H$, R=Et) | >3000 |

LD50 values were determined by the method of Miller and Tainter (Vallette, G. (1966) Manual of Pharmacodynamics. Masson et Cie, Eds. Paris, VIe, pg. 70).

Pharmacokinetics

Figure 2:
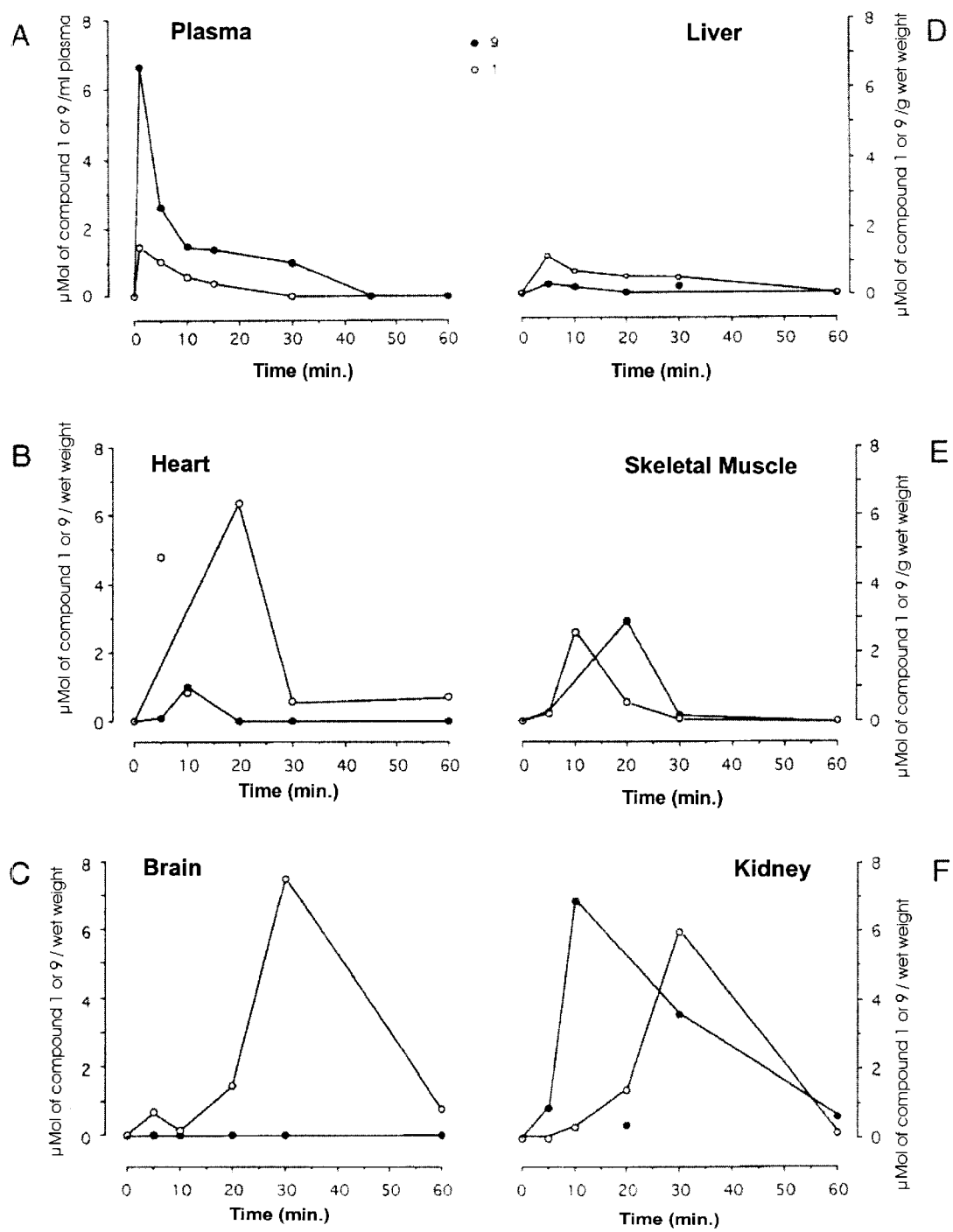

FIG. 2 (panels A–F) shows the changes in compounds 1 ($R^1=R^2=H$) and 9 ($R^1=R^2=H$, R=Et) concentration in plasma and several other tissues, as a function of time, following 1 mmol administration of these compounds to adult rats. For the experiment depicted in panel 2A, 0.5 ml of a 2 mM solution of either compound 1 ($R^1=R^2=H$; pH 7.0) or 9 ($R^1=R^2=H$, R=Et; pH 7.0) were injected into the right jugular vein of male Wistar rats (277–312 g body weight); blood samples (0.2 ml) were taken from the left jugular vein before and 1, 5, 10, 15, 30, 45 and 60 minutes after injection. The corresponding plasma samples were prepared, lyophilised, resuspended in 0.5 ml $D_2O$ (99.9%D) and then analyzed by $^1$H NMR (360, 13 MHz, 22° C., pH 7.2).

Compound 1 ($R^1=R^2=H$) clearance rate from plasma was slower ($t_{1/2}$=17 min) than that of compound 9 ($R^1=R^2=H$, R=Et; $t_{1/2}$=6 min). The highest concentrations of compounds 1 ($R^1=R^2=H$, 1.5 mM) and 9 ($R^1=R^2=H$, R=Et, 6.6 mM) were attained 2 and 1 minutes, respectively, after the injection. No signs of toxicity were detected during the experiment.

Panels 2B–2F display the kinetics of uptake of compounds 1 ($R^1=R^2=H$) and 9 ($R^1=R^2=H$, R=Et) by different tissues. In these experiments, 1 mmol of either compound 1 ($R^1=R^2=H$) or 9 ($R^1=R^2=H$, R=Et) was injected at time 0 into the right jugular vein of Wistar rats (adult males, 250–300 g body weight). Animals were sacrificed at different times after injection, in order to isolate the organs of interest as indicated in the panels; organ extracts of metabolites soluble in perchloric acid (6%) were prepared and analyzed by 1H NMR (360, 13 MHz, 22° C., pH 7.2) as previously described (Gil, M. S., Cruz, F., Cerdan, S. and Ballesteros, P. (1992) *Bioorg. Med. Chem. Lett.* 2, 1117–1722). The compound concentrations within each tissue were determined by comparing the intensities of the compound imidazolic protons with those of the TSP resonance used as internal reference (1 mM), correcting in all cases for the amount of sample tissue.

Compound 1 ($R^1=R^2=H$) was present in all tissues analysed, reaching relatively high concentrations ($\mu$mol/g of body weight) in brain (15.1), heart (12.1), skeletal muscle (5.3), kidney (12.1) and liver (2.2). Compound 1 ($R^1=R^2=H$) peak concentration in all tissues was higher than that of plasma, indicating that this compound tends to accumulate in the extracellular space. After leaving the plasma, peak concentrations of compound 1 ($R^1=R^2=H$) were attained first in liver (10 min), latter in skeletal muscle and heart (10–20 min) and last in brain and kidney (30 min). In contrast, compound 9 ($R^1=R^2=H$, R=Et) appeared to be absent from brain, trace concentrations being detected in liver (<0.2) and heart (<0.5), and it only reached concentrations similar to compound 1 ($R^1=R^2=H$) in skeletal muscle (5.8) and kidney (13.9). The trace amounts of compound 9 ($R^1=R^2=H$, R=Et) found in heart and liver most probably reflect blood contamination of these organs. Peak concentrations of compound 9 ($R^1=R^2=H$, R=Et) in tissues were reached first in kidney (at 10 min) and then in skeletal muscle (at 20 min). Compound 9 ($R^1=R^2=H$, R=Et) concentrations of a level similar to those of plasma were present only in kidney, thus indicating that this compound is a good extracellular space marker, specially for brain, liver and heart. Finally, compound 9 ($R^1=R^2=H$, R=Et) peak. concentration in kidney took place faster than that of compound 1 ($R^1=R^2=H$), but the opposite was the case in skeletal muscle.

pH Imaging by Magnetic Resonance; $^1$H CSI and $^1$H SI

Figure 3:
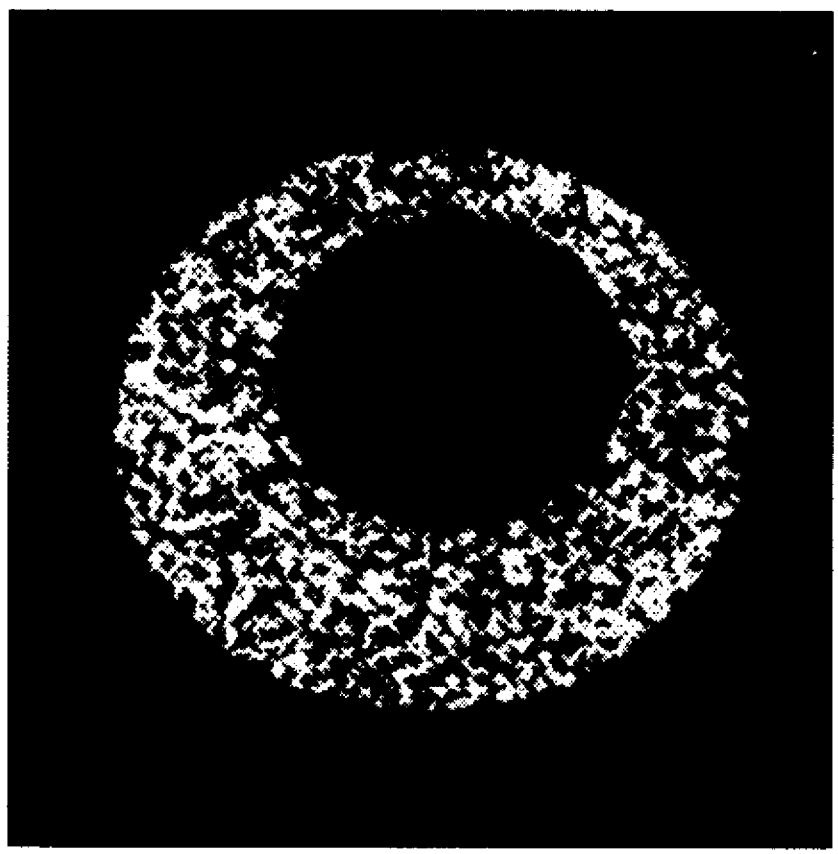

FIG. 3 shows a pH image obtained by $^1$H CSI (Chemical shift imaging) using compound 9 ($R^1=R^2=H$, R=Et). To our knowledge, this is the first image of pH spatial distribution taken with CSI techniques and an extrinsic molecular probe. In this experiment, a 0.3 mM solution of compound 9 ($R^1=R^2=H$, R=Et) in water was placed in a 5 mm NMR tube containing a 2 mm diameter water-filled capillary. An NMR image was acquired, corresponding to a coronal section perpendicular to the longest tube axis, using a commercial microimaging probe (Bruker Analistische Messtechnich, Rheinstetten, Germany) equipped with a 5 mm tube fitting and an orthogonal magnetic gradient device, actively protected against Eddy currents. The acquisition conditions were: 8.4 tesla of strength for the static magnetic field (B0), 22° C. of temperature, 500 $\mu$m slice perpendicular to the Z-axis, selective excitation of compound 9 ($R^1=R^2=H$, R=Et; 8.04 ppm) H2 resonance by spin-echo sequence and image codification of the resulting echo using a constant readout gradient (x-axis) and a variable phase gradient (y-axis), respectively (Browun, T. R., Kincaid, B. M. and Ugurbil, K. (1982) *Proc. Natl. Acad. Sci. U.S.A.*, 79, 3523–3526; Maudsley, A. A., Hilal, S. K., Perman, W. H. and Simon, H. E. (1983). *J. Mag. Res.* 66, 283–294). The chemical shift image shows that H2 resonance is present exclusively in the most outer portion of the tube, and does not contaminate, to any significant extend, the space occupied by the coaxial capillary containing only water. Given the uniform distribution of H2 resonance in the space peripheral to the capillary, it is possible to conclude that the pH value of 7.4 estimated by compound 9 ($R^1=R^2=H$, R=Et) H2 resonance is homogeneous for the entire solution. This result demonstrates that it is feasible to obtain an image of those regions of a sample with identical pH, by using CSI methods and the H2 resonance of compound 9 ($R^1=R^2=H$, R=Et). Entirely similar results can be obtained using the other probes shown in diagram 1, or alternatively extend these results using new probes with $^{19}$F together with $^{19}$F CSI.

Finally, compound 9 ($R^1=R^2=H$, R=Et) spectroscopic imaging (SI) experiments were performed in tumor-carrying mice. For that purpose, 6 to 8 week old C3H/Hen mice were backside subcutaneously inoculated with 0.5 ml of Hank's buffer containing 1×106 cells of radiation-induced fibrosarcoma (RIF-1). Tumors were allowed to grow for 1–2 weeks to a final volume of 400–900 mm3, as determined by orthogonal 3-D tumor measurements. As a preparation for the spectroscopic imaging experiment, mice received an intraperitoneal injection of compound 9 ($R^1=R^2=H$, R=Et; 0.5 ml of 1 M solution, pH 7.0). Two to five minutes after injection, mice were anesthetized with cetamine (50 mg/Kg) and acepromazine (5 mg/Kg), and then immobilised in an animal stretcher equipped with a $^1$H solenoid coil suitable to be used in the horizontal magnet of 4.7 Teslas. A warm, recirculating water bag placed under the anesthesized mice helped to maintain their body temperature constant.

Both the animal stretcher and the $^1$H coil are designed for general $^1$H spectroscopy and imaging, and do not present any characteristic which may be considered specific to the use of imidazol derivatives as extracellular pH probes. Any other equivalent probe or design can be used as easily for this purpose. The spectroscopic image was acquired using the BASSALE sequence (Shungu, D. C. and Glickson, J. D. (1993) *Mag. Res. in Med.* 30, 661–71; Shungu, D. C. and Glickson, J. D. (1994) *Mag. Res. in Med.* 32, 277–84).

Figure 4:
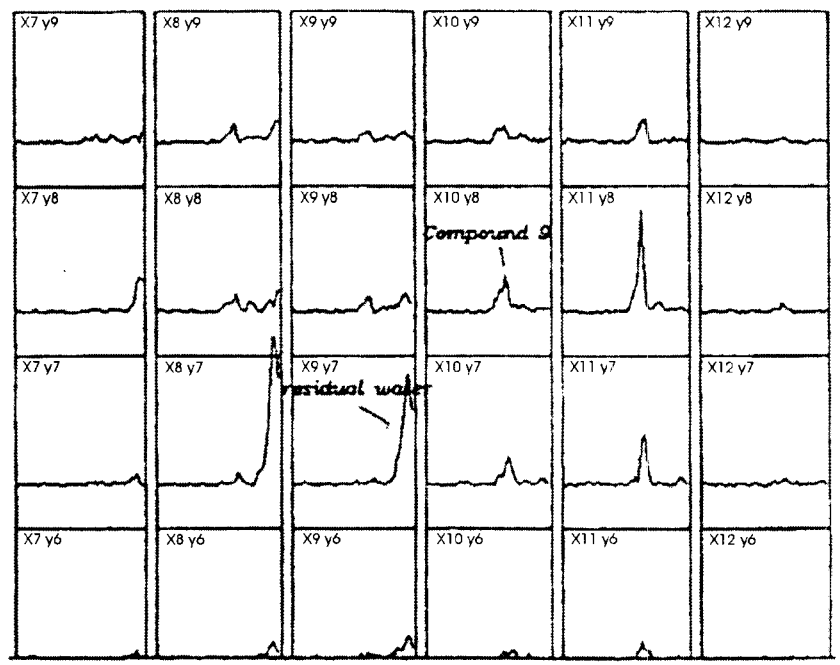
Figure 4:
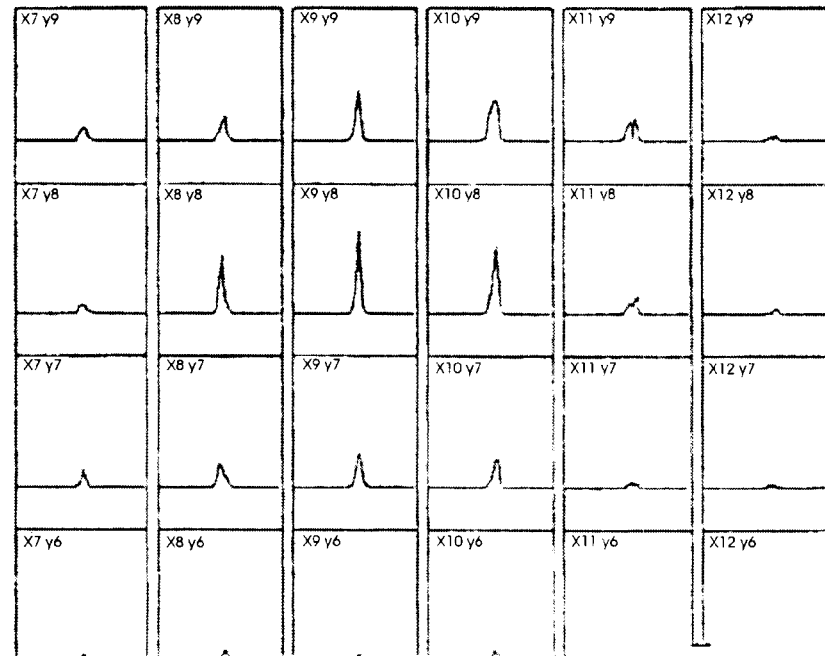

The spectroscopic image (SI) shown in FIG. 4 was obtained using voxels of 2×2×4 mm$^3$. Each spectrum (x1, y1) to (x12, y12) represents a different voxel within the tumor. The upper side (12 ppm–5.5 ppm) displays the spatial distribution of one of the resonances of compound 9 ($R^1=R^2=H$, R=Et) imidazolic protons (see voxels x10-y8, x11-y8, x10-y7 and x11-y7). The lower side shows the resonance distribution of water (at 4.7 ppm) for the same voxels.

A pH value for each voxel can be calculated from the upper side spectra and the chemical shift titration curves of compound 9 ($R^1=R^2=H$, R=Et) versus pH (20, see FIG. 1). Considering that the chemical shifts of this proton are not the same in each voxel, and that compound 9 ($R^1=R^2=H$, R=Et) remains in the extracellular space, variations in compound 9 chemical shift in between voxels reflect pH heterogeneity in different areas of the tumor.

In summary, the results presented in this patent demonstrate a new procedure for imaging extracellular pH distribution in non-transparent biological samples, using a novel series of extrinsic indicators in conjunction with Magnetic Resonance methods. We show that some of these indicators are not toxic and do allow pH determinations by Chemical shift Imaging (CSI) or Spectroscopic Imaging (SI) methods, in volumes of up to 0.2 $\mu$l with a pixel resolution of 20×20 $\mu$m in a magnetic field of 8.4 Teslas. The results derived from applying this method in vivo to tumor carrying mice are the first evidence of in situ pH heterogeneity in RIF-1 tumors implanted to C3H/Hen mice.

DETAILED DESCRIPTION OF DRAWINGS

FIG. 1. Compound 9 ($R^1=R^2=H$, R=Et) titration curve in $D_2O$ (99.9%D). H2 proton chemical shifts (δ) were measured by $^1H$ MRS (360.13 MHz, 22° C.) with respect to an internal TSP at 0 ppm. pH measurements have not been corrected for the effect of D.

FIG. 2. Compounds 1 ($R^1=R^2=H$; open circles) and 9 ($R^1=R^2=H$, R=Et; solid circles) plasma and tissue concentrations after 1 mmol intravenous injection of each compound to male Wistar rats. A: Plasma, B: Liver, C: Heart, D: Skeletal muscle (left gastrocnemius), E: Brain and F: Kidney.

FIG. 1.
Compound 9.
Chemical shift (δ)
FIG. 2.
A. Plasma
μmol of compound 1 or 9/ml plasma
Time (min.)
B. Heart
μmol of compound 1 or 9/wet weight
Time (min.)
C. Brain
μmol of compound 1 or 9/wet weight
Time (min.)
D. Liver
μmol of compound 1 or 9/g wet weight
Time (min.)
E. Skeletal Muscle
μmol of compound 1 or 9/g wet weight
Time (min.)
F. Kidney
μmol of compound 1 or 9/wet weight
Time (min.)
FIG. 3.
pH image obtained by $^1H$ CSI using Compound 9.
FIG. 4.
Spectroscopic image obtained from Compound 9.

What is claimed is:

1. A method of obtaining extracellular or intracellular pH images in a biological system by magnetic resonance, the method comprising administering to said biological system a suitable amount of an imidazole compound selected from the group consisting of

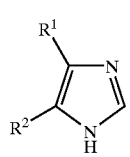
(Compound 1)

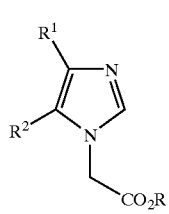
(Compound 2)

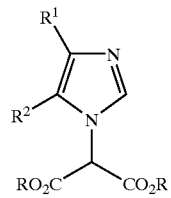
(Compound 3)

-continued

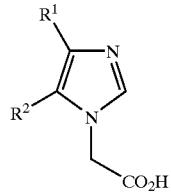
(Compound 4)

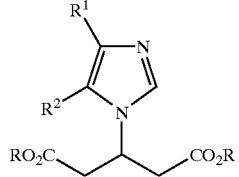
(Compound 5)

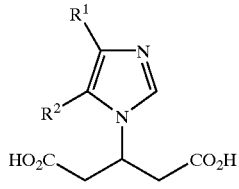
(Compound 6)

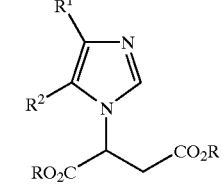
(Compound 7)

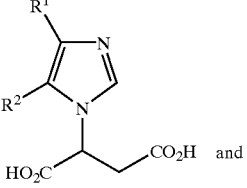
(Compound 8)

and

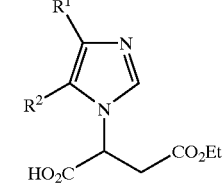
(Compound 9)

wherein
  $R^1$ and $R^2$ are H or an alkyl substituent which may comprise $^{19}F$; and
  R is alkyl;
and detecting pH by performing magnetic resonance measurement using a method selected from the group consisting of proton magnetic resonance chemical shift imaging ($^1H$ CSI), proton magnetic resonance spectroscopic imaging ($^1H$ MRSI), fluorine magnetic resonance chemical shift imaging ($^{19}$F CSI), fluorine magnetic resonance spectroscopic imaging ($^{19}$F MRSI), and combinations thereof to obtain a pH image.

2. The method of claim 1 wherein said imidazole compound is used as an extrinsic indicator for obtaining extracellular pH images.

3. The method of claim 1 comprising entrapping the imidazole compound within the intracellular space and subjecting the intracellular space to magnetic resonance measurement.

4. The method of claim 1 wherein the imidazole compound is selected from imidazole compounds where $R^1$ and $R^2$ are H and R is Et.

5. The method of claim 3 wherein the imidazole compound is selected from imidazole compounds where $R^1$ and $R^2$ are H and R is Et.

6. The method of claim 1, wherein the imidazole compound is

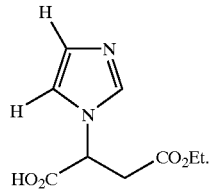

7. The method of claim 3, wherein the imidazole compound is

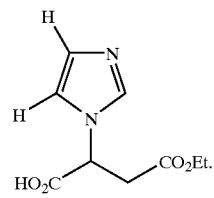

8. A method of claim 1 wherein the pH image is extracellular pH and is indicative of a physiopathology in the biological system of any of microorganisms, subcellular organelles, isolated cells, cultured cells, perfused organs, intact animals and human beings.

9. A method of claim 8 wherein the extracellular pH is indicative of a modification in the biological system causing modification of intra and extracellular pH resulting from physiological, pathological or therapeutical situations.

10. A method of claim 9 wherein the extracellular pH is modified as a result of any of muscular dystrophies, ischemic pathologies, response to therapies; benign or malignant tumor transformation, metastasis, and tumoral response to therapies.

11. A method of claim 1 wherein the pH image is intracellular pH and is indicative of a physiopathology in the biological system of any of microorganisms, subcellular organelles, isolated cells, cultured cells, perfused organs, intact animals and human beings.

12. A method of claim 11 wherein the intracellular pH is modified as a result of physiological, pathological, or therapeutic situations.

13. A method of claim 11 wherein the intracellular pH is modified as a result of muscular dystrophies, ischemic pathologies, response to therapies; benign or malignant tumor transformation, metastasis, and tumoral response to therapies.

* * * * *

UNITED STATES PATENT AND TRADEMARK OFFICE
CERTIFICATE OF CORRECTION

PATENT NO. : 6,596,258 B1
DATED : July 22, 2003
INVENTOR(S) : Paloma Ballesteros Garcia et al.

It is certified that error appears in the above-identified patent and that said Letters Patent is hereby corrected as shown below:

<u>Title page,</u>
Item [73], Assignee, add the following Assignees:
-- CONSEJO SUPERIOR DE INVESTIGACIONES CIENTIFICAS, Madrid (Spain); THE ARIZONA BOARD OF REGENTS ON BEHALF OF THE UNIVERSITY OF ARIZONA, A BODY CORPORATE IN THE STATE OF ARIZONA, Tucson, Arizona (US); THE JOHN HOPKINS UNIVERSITY SCHOOL OF MEDICINE, Baltimore, MD (US) --

Signed and Sealed this

Twenty-fifth Day of November, 2003

JAMES E. ROGAN
*Director of the United States Patent and Trademark Office*